United States Patent
Baek et al.

(10) Patent No.: US 9,434,664 B2
(45) Date of Patent: Sep. 6, 2016

(54) PREPARATION METHOD FOR EDGE-FLUORINATED GRAPHITE VIA MECHANIC-CHEMICAL PROCESS

(71) Applicant: UNIST ACADEMY-INDUSTRY RESEARCH CORPORATION, Ulsan (KR)

(72) Inventors: Jong-Beom Baek, Ulsan (KR); In-Yup Jeon, Ulsan (KR)

(73) Assignee: UNIST (ULSAN NATIONAL INSTITUTE OF SCIENCE AND TECHNOLOGY), Ulsan (KR)

( * ) Notice: Subject to any disclaimer, the term of this patent is extended or adjusted under 35 U.S.C. 154(b) by 0 days.

(21) Appl. No.: 14/605,716

(22) Filed: Jan. 26, 2015

(65) Prior Publication Data

US 2015/0210616 A1  Jul. 30, 2015

(30) Foreign Application Priority Data

Jan. 27, 2014  (KR) .................. 10-2014-0009712

(51) Int. Cl.
| | |
|---|---|
| *C07C 17/007* | (2006.01) |
| *B82Y 30/00* | (2011.01) |
| *B82Y 40/00* | (2011.01) |
| *C07C 17/02* | (2006.01) |
| *C07C 17/013* | (2006.01) |

(52) U.S. Cl.
CPC .............. *C07C 17/02* (2013.01); *B82Y 30/00* (2013.01); *B82Y 40/00* (2013.01); *C07C 17/007* (2013.01); *C07C 17/013* (2013.01)

(58) Field of Classification Search
CPC ... C07C 17/007; C07C 17/013; B82Y 30/00; B82Y 40/00
See application file for complete search history.

(56) References Cited

U.S. PATENT DOCUMENTS

| | | | | |
|---|---|---|---|---|
| 4,593,132 A | * | 6/1986 | Kita .................. | D01F 11/129 570/150 |
| 2013/0018204 A1 | * | 1/2013 | Jeon .................. | C01B 31/04 562/89 |

FOREIGN PATENT DOCUMENTS

| | | | |
|---|---|---|---|
| JP | S5969412 A | * | 4/1984 |
| KR | 10-1245815 | | 3/2013 |

OTHER PUBLICATIONS

JPS5969412A, Apr. 1984, p. 1; English Abstract.*
JPS59-069412, Apr. 19, 1984, pp. 1-6; English translation.*
Guerin, K., et al., "Synthesis and Characterization of Highly Fluorinated Graphite Containing sp2 and sp3 Carbon," Chem. Mater. 2004, vol. 16, pp. 1786-1792.

* cited by examiner

*Primary Examiner* — Fereydoun G Sajjadi
*Assistant Examiner* — Medhanit Bahta
(74) *Attorney, Agent, or Firm* — Duane Morris LLP; J. Rodman Steele, Jr.; Gregory M. Lefkowitz

(57) ABSTRACT

Disclosed is a method for producing edge-functionalized graphite or graphene with fluoro groups. According to the method, graphite is pulverized into smaller pieces and is then allowed to react with a surrounding material containing fluorine or a fluorocarbon compound. The method enables the production of graphite or graphene functionalized with fluoro groups, which could not be achieved by conventional mechanochemical methods. In addition, the method is carried out in a very simple and economical manner and is suitable for large-scale production.

10 Claims, 2 Drawing Sheets

PREPARATION METHOD FOR EDGE-FLUORINATED GRAPHITE VIA MECHANIC-CHEMICAL PROCESS

CROSS-REFERENCE TO RELATED APPLICATIONS

This application claims priority under 35 U.S.C. §119 to Korean Patent Application No. 10-2014-0009712 filed on Jan. 27, 2014 in the Korean intellectual Property Office, the disclosure of which Is incorporated herein by reference in its entirety.

BACKGROUND OF THE INVENTION

1. Field of the Invention

The present invention relates to a method for producing edge-functionalized graphite or graphene with fluoro groups via a mechanical process.

2. Description of the Related Art

Graphene has attracted attention as the most promising new material due to its excellent physical and electrical properties. There have been a number of reports on methods for the production of graphene with outstanding physical properties. Such methods can be classified into, for example, mechanical exfoliation, chemical exfoliation, exfoliation-reintercalation-expansion, chemical vapor deposition, epitaxial synthesis, and chemical synthesis.

Although mechanical exfoliation allows graphene to possess its own excellent characteristics, there is a disadvantage in that the final yield of graphene is extremely low. For this reason, the application of mechanical exfoliation is limited to studies on the characterization of graphene in laboratory.

Graphene produced by chemical vapor deposition was reported to exhibit excellent characteristics. However, chemical vapor deposition requires the use of heavy metal catalysts, involves very complicated processing steps, and is disadvantageous from an economic viewpoint, limiting its use for mass production.

Epitaxial synthesis causes poor electrical properties of graphene and requires very expensive substrates.

Chemical synthesis is the most commonly used method for graphene production. According to this method, graphite is chemically oxidized, the graphite oxide is subjected to sonication to obtain graphene oxide, and the graphene oxide is reduced to graphene. Functionalization of the graphite oxide over the entire area leads to poor physical and electrical properties of the graphite oxide. Further, it is difficult to predict to what extent and with what kind of functional groups the graphite oxide is functionalized, and as a result, a secondary reaction of the graphite oxide is substantially impossible to predict. Furthermore, the final product graphene produced from the oxidized graphite loses its excellent characteristics, which limits its use in various application fields, such as transparent electrodes.

Korean Patent No. 10-1245815, issued to the present inventors, discloses a method for producing edge-functionalized graphite via a mechanochemical process, the method including mechanically pulverizing graphite in the presence of one or more surrounding materials. This method enables the production of graphene on a large scale and the introduction of various kinds of functional groups at the edges of graphite. However, the method was not applicable to the production of graphite in which fluoro groups are introduced at the edges by using fluorine or a fluorocarbon compound.

SUMMARY OF THE INVENTION

The present invention is intended to provide a method for producing edge-functionalized graphite with fluoro groups.

The present invention is also intended to provide a method for producing edge-functionalized graphene with fluoro groups.

The present invention provides a method for producing edge-functionalized graphite or graphene with fluoro groups, including mechanically pulverizing graphite under vacuum or an inert atmosphere and reacting the pulverized graphite with fluorine or a fluorocarbon compound.

The pulverization of graphite and the reaction with fluorine or a fluorocarbon compound are preferably carried out in an atmosphere isolated from the external environment.

The pulverized graphite is preferably allowed to react with a mixture of the fluorine or fluorocarbon compound and an inert gas.

The inert atmosphere is preferably created by at least one inert gas selected from argon, helium, and neon.

The fluorocarbon compound is preferably represented by $C_aH_bX_cF_d$ wherein X is a chlorine, bromine or iodine atom, a is an integer from 1 to 6, b is an integer from 0 to 8, c is an integer from 0 to 8, d is an integer from 2 to 12, and a and d satisfy the relation a≤d. The fluorocarbon compound may be, for example, trifluoromethane, tetrafluoromethane, trifluoroethane, tetrafluoroethane, chlorotrifluoroethane, dichlorodifluoroethane, pentafluoroethane, hexafluoroethane or a mixture thereof.

The graphite is preferably pulverized at a rate of 100 to 10,000 rpm for 1 to 100 hours.

The pulverized graphite is preferably allowed to react with the fluorine or fluorocarbon compound at a pressure of 1 to 20 bar for 1 to 100 hours.

The pulverized graphite is preferably at least 50 nm in average diameter.

The fluoro groups are preferably present in an amount of 0.01 to 50% by weight, based on the total weight of the edge-functionalized graphite.

According to the method of the present invention, graphite is pulverized into smaller pieces and is then allowed to react with a surrounding material containing fluorine or a fluorocarbon compound to produce edge-functionalized graphite with fluoro groups. The method of the present invention has advantages in that the production procedure is very simple, economical, and suitable for large-scale production.

In addition, the method of the present invention enables the production of graphite or graphene functionalized with fluoro groups, which could not be achieved by the method of Korean Patent No. 10-124815 in which graphite is mechanically pulverized in the presence of surrounding materials.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE INVENTION

Figure 1:
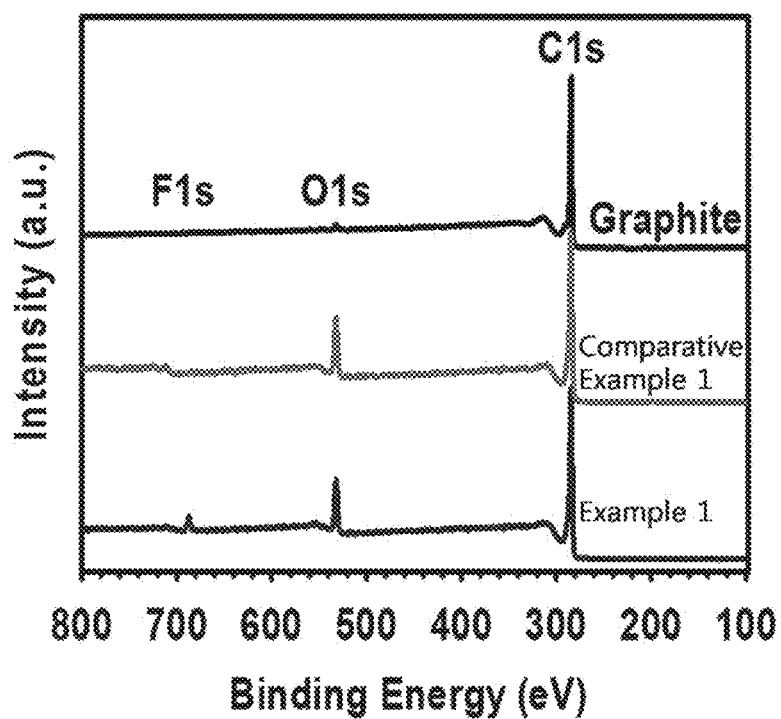
FIG. 1 shows X-ray photoelectron spectra of a graphite sample before reaction and samples of Comparative Example 1 and Example 1, which were measured to confirm the presence of a peak for fluorine on the sample surfaces in Experimental Example 1.

The present invention provides a method for producing edge-functionalized graphite or graphene with fluoro groups, including mechanically pulverizing graphite under vacuum or an inert atmosphere and reacting the pulverized graphite with fluorine or a fluorocarbon compound.

It is preferred to carry out the pulverization of graphite and the reaction with fluorine or a fluorocarbon compound in an atmosphere isolated from the external environment. As the pulverization proceeds, the edge carbons of the graphite are charged or are present in the form of radicals. The charged carbons or carbon radicals react with the surrounding liquid or gaseous compound or the surrounding solid, liquid or gaseous compound. As a result, the edges of the graphite are functionalized with fluoro groups during or after the pulverization while maintaining under vacuum or in an inert atmosphere.

If the pulverization is performed in an atmosphere that is not isolated from the external environment, the edge charged carbons or carbon radicals of the graphite react preferentially with the external environment, making it impossible to functionalize the edges of the graphite with fluoro groups despite subsequent addition of the fluorine or fluorocarbon compound. Further, if the graphite is pulverized in a fluorine or fluorocarbon compound atmosphere, a sufficiently high energy to induce bonding between the fluorine and the carbon is not generated, making it impossible to functionalize the edges of the graphite with fluoro groups.

The fluorine or fluorocarbon compound may be used in admixture with an inert gas due to its high reactivity.

The inert atmosphere for the pulverization of the graphite may be created by argon, helium or neon, and the inert gas mixed with the fluorine or fluorocarbon compound may be argon, helium or neon.

The fluorocarbon compound is preferably represented by $C_aH_bX_cF_d$ wherein X is a chlorine, bromine or iodine atom, a is an integer from 1 to 6, b is an integer from 0 to 8, e is an integer from 0 to 8, d is an integer from 2 to 12, and a and d satisfy the relation a≤d. The fluorocarbon compound may be, for example, trifluoromethane, tetrafluoromethane, trifluoroethane, tetrafluoroethane, chlorotrifluoroethane, dichlorodifluoroethane, pentafluoroethane, hexafluoroethane or a mixture thereof.

The graphite and the fluorine or fluorocarbon compound are in a molar ratio of 1:0.1 to 1:20, preferably 1:1 to 1:10. If the proportion of the graphite is more than the upper limit, the final graphite or graphene may not be sufficiently functionalized at its edges, resulting in a remarkable reduction in the production yield of the functionalized graphite or graphene.

In the method of the present invention, a container made of any material may be used to pulverize the graphite therein. The use of a container made of a metal is particularly preferred. Depending on the material for the container, impurities derived from the container material during the graphite pulverization may be incorporated in the final product. Thus, the method of the present invention may further include removing the impurities from the final product after the graphite pulverization.

For example, in the case where the graphite is pulverized in a metal container, an aqueous acid solution may be used to remove the metal.

The acid may be hydrochloric acid, sulfuric acid, nitric acid, carbonic acid, phosphoric acid, acetic acid or perchloric acid having a pH not higher than 3. The acid is preferably hydrochloric acid, sulfuric acid or nitric acid. The acid is present at a molar concentration in the range of 0.1 M to 5 M, preferably 0.5 M to 2 M, which corresponds to that of a weak acid. This range is preferred for the production of functionalized graphite.

The graphite is pulverized at a rate of 100 to 10,000 rpm for 1 to 100 hours, preferably at a rate of 100 to 2,000 rpm for 24 to 72 hours.

The pulverized graphite is preferably allowed to react with the fluorine or fluorocarbon compound at a pressure of 1 to 20 bar, preferably 2 to 15 bar, for 1 to 100 hours, preferably 12 to 64 hours.

According to the method of the present invention, as the pulverization proceeds, the edge carbons of the graphite are charged or are present in the form of radicals, which react with the surrounding fluorine or fluorocarbon compound to produce edge-functionalized graphite or graphene with fluoro groups.

According to the method of the present invention, graphene monolayers, laminates of 1 to 20 graphene sheets, preferably 2 to 15 graphene sheets, that is, graphene nanoplates, or a mixture thereof can be produced.

Preferably, the edge-functionalized graphite or graphene with fluoro groups has an average diameter of at least 50 nm.

The functional groups bonded to the edges of the functionalized graphite or graphene are preferably present in an amount of 0.01 to 50% by weight, based on the total weight of the edge-functionalized graphite.

The edge-functionalized graphite or graphene with fluoro groups may be a graphene nanoplate having a laminate structure of 1 to 20 graphene sheets.

The present invention will be explained in more detail with reference to the following examples. These examples are provided to assist in understanding the invention and the scope of the invention is not limited thereto.

Comparative Example 1

Pulverization in Fluorine Atmosphere 5 g of graphite (99%, 100 mesh) was placed into a pulverization container made of a metal. Air was evacuated from the pulverization container using a vacuum pump, a mixture of fluorine and argon was fed at a pressure of 5 bar, and the graphite was pulverized at about 500 rpm for 48 h. After completion of the pulverization, the pulverized graphite was treated with 1 M hydrochloric acid to remove the metal, followed by freeze-drying to obtain graphene nanoplates.

Example 1

Reaction with Fluorine After Pulverization 5 g of graphite (99%, 100 mesh) was placed into a pulverization container made of a metal. Air was evacuated from the pulverization container using a vacuum pump, argon gas was fed at a pressure of 10 bar, and the graphite was pulverized at about 500 rpm for 48 h. After completion of the pulverization, the argon gas was removed, and a mixture of fluorine and argon was fed at a pressure of 5 bar. After standing for 24 h, unreacted gases were removed. The obtained product was treated with 1 M hydrochloric acid to remove the metal therefrom, followed by freeze-drying to obtain graphene nanoplates functionalized with fluoro groups.

5 g of graphite (99%, 100 mesh) was placed into a pulverization container made of a metal. Air was evacuated from the pulverization container using a vacuum pomp, argon gas was fed at a pressure of 10 bar, and the graphite was pulverized at about 500 rpm for 48 h. After completion of the pulverization, the argon gas was removed and tetrafluoromethane ($CF_4$) was fed at a pressure of 2 bar. After standing for 24 h, unreacted gases were removed. The obtained product was treated with 1 M hydrochloric acid to remove the metal therefrom, followed by freeze-drying to obtain graphene nanoplates functionalized with fluoro groups.

Experimental Example 1

X-Ray Photoelectron Spectroscopy

X-ray photoelectron spectroscopy was used to analyze the surface characteristics (e.g., surface compositions) of the graphite sample of Comparative Example 1 or Example 1 before the reaction and the graphite samples of Comparative Example 1 and Example 1 after the reaction. Specifically, after X-rays were irradiated onto the surface of each sample, the energy of photoelectrons emitted from the sample-surface was measured.

As a result, a peak for the fluorine at 686 eV was observed only in the graphite sample of Example 1 and the edges of the graphite of Comparative Example 1 were not functionalized with fluoro groups (FIG. 1).

Energy dispersive X-ray spectroscopy was used to determine whether fluorine atoms were present in the graphite samples of Example 1 and Example 2. The results are shown in FIGS. 2 and 3.

Figure 2:
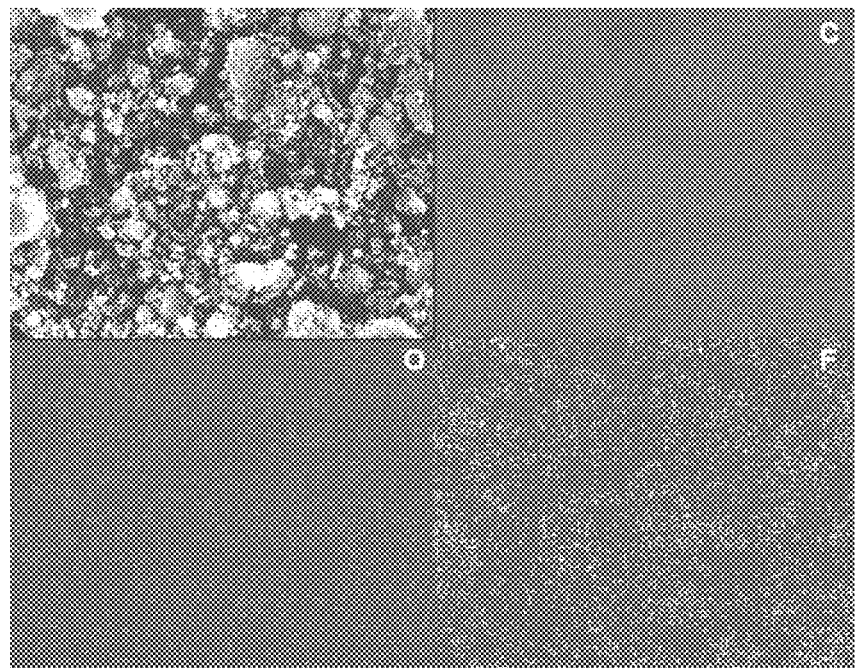
FIG. 2 shows images confirming the presence of fluorine on the surface of a sample of Example 1, which were obtained by energy dispersive X-ray spectroscopy in Experimental Example 2, the top left image is a SEM image, the top right image (C) shows the distribution of carbon atoms, the bottom left image (O) shows the distribution of oxygen atoms, and the bottom right image (F) shows the distribution of fluorine atoms.

In FIG. 2, the top left image is a SEM image of the graphite sample of Example 1. The SEM image shows that the graphite was functionalized with fluoro groups at its edges, formed planar aggregates, and had an average size at a level of 500 nm. The top right image (C) shows the distribution of carbon atoms, which are marked by red dots. The Image (C) reveals the presence of carbon atoms in the graphite sample. The bottom left image (O) shows the distribution of oxygen atoms, which are marked by green dots. The bottom right image (P) shows the distribution of fluorine atoms, which are marked by yellow dots. The Image (F) reveals the presence of fluorine atoms k the graphite sample.

Figure 3:
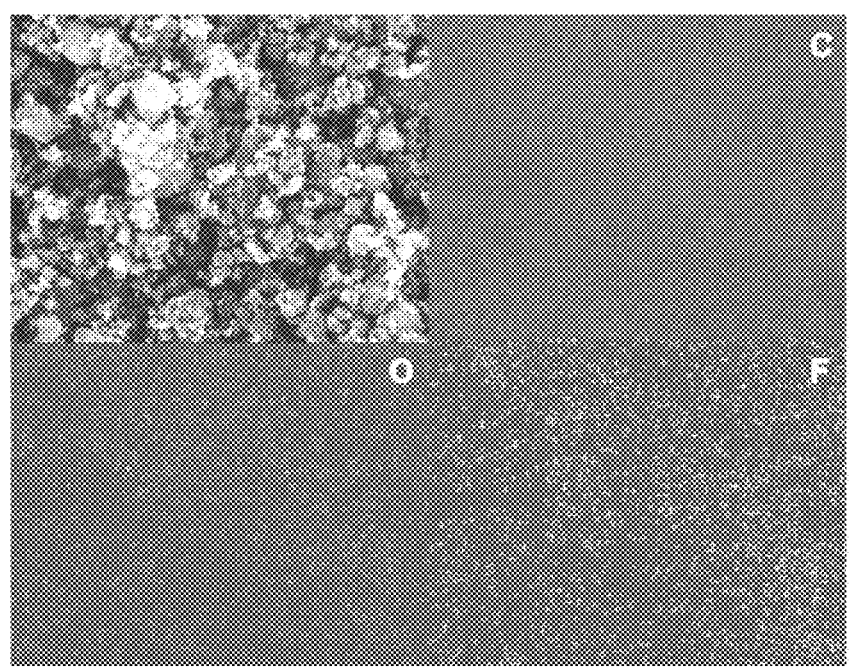
FIG. 3 shows images confirming the presence of fluorine on the surface of a sample of Example 2, which were obtained by energy dispersive X-ray spectroscopy in Experimental Example 2, the top left image is a SEM image, the top right Image (C) shows the distribution of carbon atoms, the bottom left image (O) shows the distribution of oxygen atoms, and the bottom right image (F) shows the distribution of fluorine atoms.

In FIG. 3, the top left image is a SEM image of the graphite sample of Example 2. The SEM image shows that the graphite was functionalized with fluoro groups at its edges, formed planar aggregates, and had an average size at a level of 500 nm. The top right image (C) shows the distribution of carbon atoms, which are marked by red dots. The image (C) reveals the presence of carbon atoms in the graphite sample. The bottom left image (O) shows the distribution of oxygen atoms, which are marked by green dots. The bottom right image (F) shows the distribution of fluorine atoms, which are marked by yellow dots. The image (F) reveals the presence of fluorine atoms in the graphite sample.

As is apparent from the foregoing, the method of the present invention has a very high possibility of commercialization due to its high environmental friendliness.

The prior art method for producing graphite oxide enables the functionalization of graphite at its central area as well as its edges, while the method of the present invention enables the functionalization of graphite only at its edges. Therefore, functionalized graphite produced by the method of the present invention has excellent physical and electrical properties compared to functionalized graphite oxide produced by the prior art method.

Edge-functionalized graphite or graphene produced by the method of the present invention can be considered a promising new precursor that can promote the practical application of graphite or graphene.

What is claimed is:

1. A method for producing edge-functionalized graphite or graphene with fluoro groups, comprising (i) mechanically pulverizing graphite under an inert atmosphere in a closed container; (ii) then, evacuating the inert atmosphere, and (iii) reacting the pulverized graphite with fluorine or a fluorocarbon compound at a pressure of 2 to 20 bar, wherein the fluorocarbon compound is trifluoromethane, tetrafluoromethane, trifluoroethane, tetrafluoroethane, chlorotrifluoroethane, dichlorodifluoroethane, pentafluoroethane, hexafluoroethane or a mixture thereof.

2. The method according to claim 1, wherein the pulverization of graphite and the reaction with fluorine or a fluorocarbon compound are carried out in an atmosphere isolated from the external environment.

3. The method according to claim 1, wherein step (iii) further comprises introducing an inert gas and the pulverized graphite is allowed to react with a mixture of the fluorine or fluorocarbon compound in the presence of the inert gas.

4. The method according to claim 1, wherein the inert atmosphere is created by at least one inert gas selected from the group consisting of argon, helium, and neon.

5. The method according to claim 1, wherein the graphite is pulverized at a rate of 100 to 10,000 rpm for 1 to 100 hours.

6. The method according to claim 1, wherein the pulverized graphite is allowed to react with the fluorine or fluorocarbon compound for 1 to 100 hours.

7. The method according to claim 1, wherein the pulverized graphite is 50 nm or more in average diameter.

8. The method according to claim 1, wherein the fluoro groups are present in an amount of 0.01 to 50% by weight, based on the total weight of the edge-functionalized graphite.

9. The method according to claim 1, wherein the edge-functionalized graphite or graphene with fluoro groups is a graphene nanoplate having a laminate structure of 1 to 20 graphene sheets.

10. The method according to claim 1, comprising reacting the pulverized graphite with fluorine or a fluorocarbon compound at a pressure of 2 to 15 bar.

* * * * *